United States Patent [19]

Rosini et al.

[11] Patent Number: 4,621,077

[45] Date of Patent: Nov. 4, 1986

[54] PHARMACOLOGICALLY ACTIVE BIPHOSPHONATES, PROCESS FOR THE PREPARATION THEREOF AND PHARMACEUTICAL COMPOSITIONS THEREFROM

[75] Inventors: Sergio Rosini; Giorgio Staibano, both of Pisa, Italy

[73] Assignee: Istituto Gentili S.p.A., Pisa, Italy

[21] Appl. No.: 618,578

[22] Filed: Jun. 8, 1984

Related U.S. Application Data

[63] Continuation-in-part of Ser. No. 480,264, Mar. 30, 1983.

[30] Foreign Application Priority Data

Apr. 15, 1982 [IT]  Italy ............................... 20781 A/82

[51] Int. Cl.$^4$ .............................................. A61K 31/66
[52] U.S. Cl. .................................................... 514/108
[58] Field of Search ......................... 424/204; 514/108

[56] References Cited

U.S. PATENT DOCUMENTS

| | | | |
|---|---|---|---|
| 3,442,604 | 5/1969 | Smith et al. | 424/204 |
| 3,962,432 | 6/1976 | Schmidt-Dunker | 424/204 |
| 4,054,598 | 10/1977 | Blum et al. | 424/204 |
| 4,137,309 | 1/1979 | Van Duzee | 424/204 |
| 4,216,211 | 8/1980 | Francis | 424/204 |
| 4,216,212 | 8/1980 | Flora et al. | 424/204 |
| 4,230,700 | 10/1980 | Francis | 424/204 |
| 4,254,114 | 3/1981 | Triebwasser | 424/204 |
| 4,264,582 | 4/1981 | Flora et al. | 424/204 |
| 4,275,059 | 6/1981 | Flora et al. | 424/204 |
| 4,282,214 | 8/1981 | Flora et al. | 424/204 |
| 4,309,364 | 1/1982 | Bentzen et al. | 424/204 |
| 4,330,530 | 5/1982 | Baker | 424/204 |
| 4,330,537 | 5/1982 | Francis | 424/204 |
| 4,371,527 | 2/1983 | Bentzen et al. | 424/204 |

FOREIGN PATENT DOCUMENTS

| | | | |
|---|---|---|---|
| 57-154131 | 3/1982 | Japan | 424/204 |
| 7308017 | 12/1973 | Netherlands | 424/204 |
| 2096889 | 10/1982 | United Kingdom | 424/204 |

OTHER PUBLICATIONS

Chem. Abstract 96:52503t.
Chem. Abstract 100:175062g.
Chem. Abstract 88:170246u.
Fleisch, et al., *Europ. J. Clinical Invest.*, vol. 1, pp. 12–18 (1970).
Bassett et al., *The Yancet*, p. 845 (1969).
Francis, *Calc. Tiss. Res.*, 3, pp. 151–162 (1969).
Russell et al., *Calc. Tiss. Res.*, 6, pp. 183–196 (1970).

*Primary Examiner*—Albert T. Meyers
*Assistant Examiner*—F. Abramson
*Attorney, Agent, or Firm*—Bucknam and Archer

[57] ABSTRACT

Biphosphonic acids of general formula I:

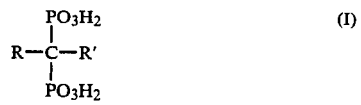

in which R is a fluorine atom of a linear or branched alkyl radical containing between 1 and 5 carbon atoms, which may also be substituted by one or more amino groups of fluorine atoms or both amino groups and fluorine atoms, R' is hydroxy or fluorine, and their salts with an alkali metal, an organic base or a basic aminoacid, exhibit valuable properties in the treatment of urolithiasis or in the treatment as inhibitors of bone reabsorption. The compound 4-amino-1-hydroxybutan-1,1-biphosphonic acid is between 100 and 300 times more active than Cl$_2$MDP.

1 Claim, No Drawings

PHARMACOLOGICALLY ACTIVE BIPHOSPHONATES, PROCESS FOR THE PREPARATION THEREOF AND PHARMACEUTICAL COMPOSITIONS THEREFROM

This application is a continuation-in-part of U.S. Ser. No. 480,264 filed Mar. 30, 1983.

The present invention relates to the preparation of biphosphonic acid and their salts. The invention also relates to pharmaceutical compositions suitable for the treatment of urolithiasis and capable of inhibiting the bone reabsorption.

It is known that condensed phosphates in low concentrations may prevent the deposition of calcium carbonate from solutions; in addition to this effect, the condensed phosphates and among them the pyrophosphate, are capable of inhibiting the precipitation of calcium phosphate when there are added even in low concentrations to solutions of calcium phosphates. This inhibitory action manifests itself both in the absence as well as in the presence of crystals of apatite.

In addition, the condensed phosphates retard the transformation of calcium phosphate from the amorphous phase to the crystalline phase without, however, influencing the formation of the amorphous phase. The marked effect in vitro of the pyrophosphate (PP) on calcium phosphate in concentrations close to the concentrations found in the biological fluids, has suggested that the pyrophosphate may protect soft tissues from mineralization. In bone, the pyrophosphate (PP) could also regulate the progress of calcification and, therefore, influence the transformation of calcium and phosphate. The PP in bone which has already been mineralized influences the movement of calcium and phosphate towards the interior and the exterior of the bone. In spite of all the knowledge which has been acquired with respect to PP, its therapeutic use results impossible bacause of the rapid hydrolysis which the substance undergoes both when it is administered by the oral route as well as when it is administered by the systemic route.

In view of the great interest connected with PP, investigation has been carried for the purpose of making substances with similar activity but resistant to hydrolysis. This object has been achieved partially with the synthesis of biphosphonates, that is substances which contain the group P-C-P instead of the group P-O-P. The action of the biphosphonates on calcium salts is similar to the action of PP; indeed, even in low concentration, they exhibit the following actions:

they inhibit the precipitation of calcium phosphate from solutions;

they block the transformation of amorphous calcium phosphate into the crystalline form without, however, inhibiting the formation of the initial phase;

they block the aggregation of crystals of hydroxyapatite;

they retard the degree of dissolution of crystals of hydroxyapatite after the latter have absorbed the biphosphonates from the solutions.

Several pharmacological and clinical studies in the scientific literature, however demonstrate that, in spite of certain analogies in activity, the several biphosphonates used up to the present time in the treatment of osteop thia exhibit some quite serious drawbacks with respect to the degree of toxicity in animals and the tolerability or the inducement of negative colateral side effects in men.

It has been now found surprisingly that some biphosphonic acids of general formula I:

in which R is fluorine or a linear or branched alkyl residue containing between 1 and 5 carbon atons, which may optionally be substituted by a substituent such as amino groups and/or fluorine atoms and R' is hydroxy or fluorine and their salts with alkali metals, organic bases and basic aminoacids are very suitable for the treatment of urolithiasis and as inhibitors of the bone reabsorption because they exhibit high activity which is not accompanied by the side effects hereinabove mentioned with respect to the pyrophosphate (PP).

Several biphosphonic acids have been described in the literature. In particular biphosphonic acids of general formula I in which R is an unsubstituted alkyl and R' is hydroxy may be prepared by reacting an acyl halide or the anhydride of an acid with phosphorous acid or phosphorous trichloride. This procedure, although it gives good yield in the case in which R is ethyl, is less suitable for the achievement of analogues containing an alkyl residue with a higher molecular weight and it is practically inoperative when the residue R is an alkyl group substituted by functional groups.

In addition, this procedure clearly is not suitable to prepare compounds of formula I in which R and/or R' are fluorine atoms. It has now been found that it is possible to prepare compounds of general formula I in which R is an amino alkyl group and R' is hydroxy with excellent yields and with a very high degree of purity when one reacts an aminoacid with phosphorous acid for the purpose of blocking the reactive amino group and then with phosphorus trichloride. The intermediate is then hydrolyzed and the product is isolated in an appropriate manner.

Instead of the mixture of phosphorous acid and phosphorus trichloride, it is possible to use only phosphorus trichloride adding the stoichiometric amount of water in order to form the corresponding phosphorous acid.

Whenever it is possible, the aminoacid may be replaced by a precursor capable of forming the aminoacid by hydrolysis such as valerolactam or the corresponding polyamide in the case of 5-aminovaleric acid or the pyrrolidone in the case of 4-amino-butyric acid. The reaction is preferably carried out in the presence of an aprotic organic solvent such as an aliphatic or aromatic hydrocarbon or the corresponding chlorinated hydrocarbon, but may also be carried out in the absence of a solvent.

During the reaction, there is formed a pasty solid of composition not well defined from which the desired aminobiphosphonic acid is obtained by hydrolysis with water or aqueous HCl.

The procedure described hereinabove is easily adapted to the industrial production of the acids of formula I. The preparation of the biphosphonic acids of general formula I in which R and R' are both fluorine atoms may be carried out easily and with high yields by hydrolyzing the corresponding esters of general formula II:

$$F_2C[PO(OR'')_2] \quad (II)$$

in which R" is an alkyl residue which may be linear or branched containing between 1 and 4 carbon atoms. The esters of formula II are obtained by reacting the corresponding ester of the bromodifluoromethanphosphonic acid (which is obtained from dibromodifluoromethane and a trialkylphosphite) with a dialkylphosphite of an alkali metal such as sodium according to the reaction scheme hereinbelow:

$$CF_2Br_2 + P(OR'')_3 \longrightarrow$$

$$Br-CF_2-PO(OR'')_2 \xrightarrow{NaPO(OR'')_2} II$$

The hydrolysis of the ester of formula II to the corresponding biphosphonic acid is carried out with water and mineral acid. The preferred compounds which are obtained according to the process of the present invention are:
5-amino-1-hydroxypentan-1,1-biphosphonic acid;
4-amino-1-hydroxybutan-1,1-biphosphonic acid;
difluoro-methanbiphosphonic acid;
and their sodium, aniline and lysine salts.

The following examples are described hereinbelow for the purpose of further illustration of the invention.

EXAMPLE 1

A mixture consisting of 117 grams (1.0 moles) of 5-amino-valeric acid, 123 grams (1.5 moles) of phosphorous acid and 500 cc of anhydrous chlorobenzene is prepared. The mixture is heated by means of a boiling water bath up to 100° C. in a manner to solubilize the solid almost completely. Keeping the temperature at 100° C. and under vigorous stirring, there are added slowly 206 grams (1.5 mole) of phosphorous trichloride. About 30 minutes after the end of the addition, the formation of a dense phase which has a tendency to increase and to harden with time begins. The mixture is kept for an additional three hours at 100° C. and it is then allowed to cool under stirring. In this manner, the solid material breaks up into small pieces and may be filtered and washed with chlorobenzene. The hygroscopic solid so obtained is then dissolved in 500 cc of water and is heated for one hour under reflux. After cooling, the solution is treated with active carbon and then filtered. The crude acid precipitates by addition of an excess of warm methanol and after separation, the product is crystallized from one liter of water at 100° C.

The yield is 165 grams (63% of theory) of 5-amino-1-hydroxypentan-1,1-biphosphonic acid in the form of a white crystalline powder of melting point 235° C. Elementary analysis: Found: C=22.69; H=5.71; N=5.14; P=23.70. calcd for $C_5H_{15}NO_7P_2$: C=22.82; H=5.75; N=5.32; P=23.54.

Infrared Spectrum: Absorption bands at 3220, 1660 and 1510 cm$^{-1}$.

Spectrum $^1$H-N.M.R.(TMS as a standard): $\delta=1.8$ ppm (6H); $\delta=3.0$ ppm (2H).

EXAMPLE 2

In a 150 liters glass reactor, there are introduced 9.4 kg of 5-aminovaleric acid, 9.9 kg of phosphorous acid and 40 liters of anhydrous chlorobenzene. The mixture is heated under stirring up to 90°–100° C. and 16.5 kg of phosphorus trichloride is added over a period of 30 minutes. The reaction mixture after standing at 110° C. for three hours, is cooled to 80° C. and then 50 liters of water are added so as to dissolve all the solid material. The organic phase is allowed to cool and to separate from the aqueous phase. After treatment of the aqueous phase with active carbon and filtration, excess methanol is added under stirring so as to precipitate the crude aminobiphosphonic acid. The mixture is filtered and the product is recrystallized from 60 liters of boiling water. The product is 12.4 kg of crystalline material of pure 5-amino-1-hydroxypentan-1,1-biphosphonic acid.

EXAMPLE 3

A mixture of 1 mole of 4-aminobutyric acid, 1.5 moles of phosphorous acid and 500 cc anhydrous chlorobenzene, is heated up to 100° C. At this temperature, phosphorus trichloride in the amount of 1.5 mole is added under strong stirring. The mixture is stirred at 100° C. for 3½ hours until the dense phase is completely formed and is then allowed to cool. The solid is filtered, washed with a small amount of chlorobenzene and dissolved in water. The solution is heated to the boiling point for one hour, it is then cooled and decolorized with active carbon. The material is filtered and the product is precipitated with excess of hot methanol. The crude material so obtained is heated under reflux for eight hours in 20% hydrochloric acid. The hydrochloric acid is removed by distillation and the residue is recrystallized from water. The product is 4-amino-1-hydroxybutan-1,1-biphosphonic acid in the form of a white crystalline powder which has the structure hereinbelow as shown by the properties also reported hereinbelow:

$$\begin{array}{c} (CH_2)_3NH_2 \\ | \\ H_2O_3P-C-PO_3H_2 \\ | \\ OH \end{array}$$

| | Elementary analysis | | | |
|---|---|---|---|---|
| | C % | H % | N % | P % |
| Found: | 17.88 | 5.62 | 4.93 | 23.94 |
| Calcd for ABDP: | 19.28 | 5.26 | 5.64 | 24.86 |
| Calcd for ABDP.H$_2$O: | 17.98 | 5.66 | 5.24 | 23.19 |

Determination of the Moisture Content

The sample examined according to the Karl-Fischer method has a water content of about 3.9% by weight.

Potentiometric Titration

The curve of potentiometric titration is obtained by addition of 0.1N NaOH to a solution of 203 mg of the sample dissolved in 75 cc of water. The profile of this curve is characterized by 2 clear end points at pH 4.4 and 9 corresponding to an addition of the reagent of 7.5 and 15.2 cc respectively. From the values reported, one calculates an equivalent weight of 270 for the first neutralization and 264 for the second neutralization and an average equivalent weight of 267. The molecular weight of ABDP.H$_2$O is 267.114.

Complexometric Titration

The complexometric titration is carried out with thorium nitrate with 41.47 mg of the compound. It shows a color change after an addition of 5.4 cc of the reagent. From this value, it is possible to conclude that the substance being examined has an equivalent weight of 134, which is in agreement with the presence of two phosphonic groups in the molecole of the monohydrate.

Infrared Absorption

The infrared spectrum observed on a tablet of KBr presents characteristic bands at:

3600–2500 cm$^{-1}$ complex band due the overlapping of the stretching of acidic and alcoholic OH groups, groups $NH_3^+$ and aliphatic CH.

1650, 1605, 1500 bands due the deformation of the group $NH_2$ partially in the salt form due the presence of the phosphonic groups.

1160 stretching of the P-O bond.

1040 stretching of the C-O bond.

960, 930 stretching of the P-O bond.

600–400 skeleton bands which involve substantially the portion of the molecule which contains phosphorus atoms.

Nuclear Magnetic Resonance on the Proton ($^1$H-NMR)

The $^1$H-NMR spectrum calculated in $D_2O/D_2SO_4$ presents two enlarged signals at $\delta 2.6$ ppm ($CH_2$-$\beta$ and $CH_2$-$\gamma$ due the $NH_2$ group) and 3.5 ppm ($CH_2$-$\alpha$ due the $NH_2$ group) for a relative intensity 2:1.

Nuclear Magnetic Resonance on Carbon ($^{13}$C-NMR)

The spectrum $^{13}$C-NMR determined in $D_2O/D_2SO_4$ presents signals at $\delta 20$ ppm ($CH_2$-$\beta$ due the $NH_2$ group), 28 ppm ($CH_2$-$\gamma$ due the $NH_2$ group), 39 ppm ($CH_2$-$\alpha$ due the $NH_2$ group) and a central triplet at 72 ppm (C-$\delta$ due the $NH_2$ group, $J_{C-P}$ 156 Hz).

Nuclear Magnetic Resonance on Phosphorus ($^{31}$P-NMR)

The spectrum $^{31}$P-NMR determined in the $D_2O/D_2SO_4$ presents a single signal at 9 ppm showing that two phosphorus atoms are chemically and magnetically equivalent.

EXAMPLE 4

Sodium diisopropylphosphite and diisopropyl bromodifluoromethanephosphonate are reacted according to conventional methods to produce the tetraisopropyl ester of difluoromethanebiphosphonic acid which is obtained as a colorless and odorless liquid of boiling point 117° C. (0.2 torr).

Spectrum $^{19}$F-N.M.R.: =21.6 (triplet, $CF_2$, $J_{F-P}$=86.67).

Spectrum $^{31}$P-N.M.R.: = −16.1 (triplet, $J_{F-P}$= 14.6); $H_3PO_4$ 85% as the external standard.

The ester thus obtained is hydrolyzed to difluoromethanebiphosphonic acid which is obtained in crystalline form and is dried in a vacuum desiccator over $P_2O_5$. The substance is a very hygroscopic solid of melting point 90° C.

The curve of titration acid/base presents two clear end points at pH 3.9 and 10.1 which correspond respectively to the bisodium and tetrasodium salts and a single end point at pH 6.8 which corresponds to the trisodium salt. The molecular weight corresponding to the above titration values is 210.3 (theory 211.99).

EXAMPLE 5

To a suspension of 263 grams of 5-amino-1-hydroxypentan-1,1-biphosphonic acid in one liter of water is added under cooling a solution prepared from 40 grams of sodium hydroxide in 500 cc of water. There is obtained a clear solution which after decolorization with carbon, filtration and concentration is kept in the cold for a period of three days under gentle stirring. The crystalline solid thus obtained is filtered washed with a small amount of cold water and then methanol. After drying at 100° C., there is obtained 199 grams of the monosodium salt of 5-amino-1-hydroxy-pentan-1,1-biphosphonic acid.

EXAMPLE 6

From difluoromethanebiphosphonic acid there is obtained, according to conventional methods, the trisodium difluoromethanebiphosphonate as a crystalline white powder soluble in water. The molecular weight determined by acid/base titration is 274.0 (theory 277.9). The 0.1 molar aqueous solution has pH=6.8.

Elementary analysis: Found: C=4.30; H=0.52; P=23.01; F=12.90. Calcd for $CHF_2Na_3O_6P_2$: C=4.32; H=0.36; P=22.29; F=13.67.

EXAMPLE 7

From difluoromethanebiphosphonic acid there is obtained according to conventional methods the aniline difluoromethanebiphosphonate. The substance, after recrystallization from ethanol, melts at 163°–165° C.

Elementary analysis: Found: C=50.88; H=6.02; N=9.19; P=9.90. Calcd for $C_{25}H_{32}F_2N_4O_6P_2 \cdot H_2O$ (tetraaniline salt as the monohydrate): C=50.80; H=5.57; N=9.11; P=10.08.

UV Sprectrum (in an aqueous solution): Absorption maximum at 279 nm; $\epsilon \approx 3241$.

EXAMPLE 8

From difluoromethanebiphosphonic acid there is obtained according to the method of Example 7, the lysine difluoromethanebiphosphonate. The dilysine salt, which precipitates from water, is obtained as a white amorphous powder, very soluble in water and hygroscopic. A 0.1M solution has a pH=4.0.

Elementary analysis: Found: C=30.03; H=6.42; N=10.87; P=13.01. Calcd for $C_{13}H_{32}F_2N_4O_{10}P_2$: C=30.96; H=6.39; N=11.11; P=12.28.

TOXICOLOGY STUDY

This study has been carried out with the following substances according to the present invention:

4-amino-1-hydroxybutan-1,1-biphosphonic acid (AH-B$_U$BP);

5-amino-1-hydroxypentan-1,1-biphosphonic acid (AH-P$_E$BP);

difluoromethanebiphosphonic acid as the sodium salt ($F_2$MBP).

By way of comparison the following substances have been used:

6-amino-1-hydroxyhexane-1,1-biphosphonic acid (AHE$_X$BP)

prepared according to Italian Patent Application No. 19673 A/81 dichloromethanebiphosphonic acid as the sodium salt ($Cl_2$MBP) (known).

Acute Toxicity

For this study Swiss mice, both male and female, have been utilized: during the experiment, the animals are fed according to the method with Altromin in the form of tablets. For the oral and intraperitoneal administration, there are used 5% gum arabic solutions while saline solutions of pH 4 are used for the intravenous injections.

The preliminary values of $DL_{50}$ are calculated according to a graphic method. Table 1 reports the values of the $DL_{50}$ in Swiss mice in mg/kg.

TABLE 1

| | $DL_{50}$ in Swiss Mice in mg/kg | | |
|---|---|---|---|
| | os | i.p. | i.v. |
| $AHB_UBP$ | >2,000 | — | 85 |
| $AHP_EBP$ | 1,500 | 75 | 85 |
| $AHE_XBP$ | >2,000 | 125 | 75 |
| $F_2MBP$ | >2,000 | 450 | 70 |
| $Cl_2MBP$ | >2,000 | 750 | 130 |

After the oral administration, also at the high dosage, no change in the behavior of the aninal is observed, no death is noted and the only symptom is a certain softening of the stool. The autopsy of the animal killed shows a slight change in the kidneys which are of light and anemic color.

After the intravenous injection, the animals die immediately at the high dosage with convulsions and dyspnea. At the dosage lower than the lethal dose, the convulsions are less evident and continue for a period of two hours; the animals, after returning to normal, show a few cases of death after 2–4 days with dyspnea, hair erection and reduced motor activity. The autopsies show the kidneys with a pink or yellowish color with hemorragic spots. The female animals exhibit hypertrophic and hyperemic ovaries. The conclusion is that the novel biphosphonates exhibit acute toxicity and moderate chronic toxicity.

Inhibition of the Formation of Crystals

A model system is used to evaluate the ability of the phosphonates to inhibit the formation of crystals in inorganic solutions. Three solutions are prepared according to Fleisch.

(1) 0.0107M $KH_2PO_4$; 0.117M KCl; 0.01M barbituric acid
(2) 0.0056M $CaCl_2$; 0.138M KCl; 0.01M barbituric acid
(3) 0.155M KCl; 0.01M barbituric acid.

The pH is brought to 7.4 by means of potassium hydroxide. The concentration of $Ca^{++}$ was 6.7 mg%, a level similar to the calcium in blood which has been subjected to untrafiltration and the concentration of the inorganic phosphate Pi give a product $Ca^{++} \times Pi = 80$. The solution was analyzed for $Ca^{++}$ and Pi and was distributed in Erlenmeyer flasks 12 cc each. The flasks were divided in groups as follows:

| (a) Control | |
|---|---|
| (b) $AHE_XBP$ | 0.05 μM |
| (c) $AHE_XBP$ | 0.25 μM |
| (d) $AHE_XBP$ | 0.5 μM |
| (e) $AHE_XBP$ | 2.5 μM |
| (f) $AHE_XBP$ | 5.0 μM |
| (g) $Cl_2MBP$ | 0.5 μM |
| (h) $Cl_2MBP$ | 2.5 μM |
| (i) $Cl_2MBP$ | 5.0 μM |
| (l) $F_2MBP$ | 0.5 μM |
| (m) $F_2MBP$ | 2.5 μM |
| (n) $F_2MBP$ | 5.0 μM |
| (o) $AHP_EBP$ | 0.05 μM |

| -continued | |
|---|---|
| (p) $AHP_EBP$ | 0.25 μM |
| (q) $AHP_EBP$ | 0.5 μM |
| (r) $AHP_EBP$ | 2.5 μM |
| (s) $AHP_EBP$ | 5.0 μM |
| (t) $AHB_UBP$ | 0.5 μM |
| (u) $AHB_UBP$ | 2.5 μM |
| (v) $AHB_UBP$ | 5.0 μM | and then they are incubated under stirring at 37° C. for two days.

At the end of incubation, the solutions are passed through "millipore filters" for the purpose of retaining the ctystals which are formed during the incubation; the filtrate then is analyzed for $Ca^{++}$ and Pi. The results are also reported in Table 2 as the product of $Ca^{++} \times Pi$ in the solution at the end of the experiment.

The data show that the bisphosphonates according to the present invention induce a significant inhibitory activity on the formation and growth of crystals of apatite according to a pattern which is dependent on the dose.

TABLE 2

| | Values of the product $Ca^{++} \times Pi$ in solution | | |
|---|---|---|---|
| Substance | Conc. μM | Prior to Incubation | After Incubation |
| Control | 0.0 | 114.7 | 29 |
| $Cl_2MBP$ | 0.5 | " | 44.0 |
| $Cl_2MBP$ | 2.5 | " | 60.4 |
| $Cl_2MBP$ | 5.0 | " | 73.6 |
| $F_2MBP$ | 0.5 | " | 44.6 |
| $F_2MBP$ | 2.5 | " | 58.5 |
| $F_2MBP$ | 5.0 | " | 72.0 |
| $AHE_XBP$ | 0.05 | " | 30.0 |
| $AHE_XBP$ | 0.25 | " | 37.5 |
| $AHE_XBP$ | 0.5 | " | 59.6 |
| $AHE_XBP$ | 2.5 | " | 92.6 |
| $AHE_XBP$ | 5.0 | " | 95.3 |
| $AHP_EBP$ | 0.05 | " | 36.7 |
| $AHP_EBP$ | 0.25 | " | 37.1 |
| $AHP_EBP$ | 0.5 | " | 68.6 |
| $AHP_EBP$ | 2.5 | " | 94.0 |
| $AHP_EBP$ | 5.0 | " | 97.5 |
| $AHB_UBP$ | 0.5 | " | 53.2 |
| $AHB_UBP$ | 2.5 | " | 88.6 |
| $AHB_UBP$ | 5.0 | " | 93.5 |

Pharmacological Tests

The purpose of this study is to investigate the effect of a series of novel biphosphonates on a culture of skull cells and on the bone reabsorption and the mineralization in vivo.

Methods used

1. Experiments on skull cells

Cellular culture: the cells are cultured according to the method described by Fast et al, (Biochem. J. 172, 97–107 (1978)). By way of summary, the skulls removed from Wistar rats, one day old, are digested with collagenase. The cells set free are placed on a plate with concentration of 200,000 cells per cc of medium in disks "clusters" suitable for culture, the plates having 24 wells of 1.6 cm in diameter containing 0.5 cc of medium. The cells are cultivated in the essential minimum medium containing 10% of foetal calf serum in an atmosphere of 5% $CO_2$ at 37° up to the eighth day. The bisphosphonates are added on the first day up to the end of the experiment. The medium is changed on the first, fourth and seventh day.

Cellular count

The cells are counted with a Coulter counter after they have been set free from the disks by digestion with a mixture of collagenase and trypsin.

Determination of lactate

On the seventh day, the medium is changed and the cells are incubated for 16 hours. The lactate produced during this period is measured in an extract in $HClO_4$ of the medium using lactatodehydrogenase.

2. Experiments on the bone reabsorption and in vivo calcification ing to the method of Shenk et al., Calc. Tiss. Res. 11, 196-214, 1973).

Results

1. Experiments with skull cells

As shown in Table 3, $Cl_2MBP$ causes a decrease in the number of cells. On the other hand, $F_2MBP$ has no effect or a very small effect in this respect. The aminoderivatives show a difference because the compounds with an odd number of carbon atoms decrease the cellular number to a much greater extent than the compounds with an even number of carbon atoms.

TABLE 3

| Composition | Effect on the cellular number ± S.E.M. (n) % of control concentration (μM) | | |
|---|---|---|---|
| | 2.5 | 25 | 250 |
| $Cl_2MBP$ | 103.0 ± 0.7 (4) | 86.4 ± 2.1 (12)*** | 54.5 ± 1.9 (12)*** |
| $F_2MBP$ | 88.1 ± 1.4 (12)*** | 92.4 ± 1.9 (12)** | 99.3 ± 2.0 (16) |
| $AHB_UBP$ | 100.5 ± 1.6 (8) | 101.0 ± 1.5 (7) | 74.2 ± 4.7 (15)*** |
| $AHP_EBP$ | 102.7 ± 2.8 (8) | 42.6 ± 5.1 (16)*** | dead cells |
| $AHE_XBP$ | 93.3 ± 3.0 (8)* | 95.2 ± 2.2 (8) | 87.0 ± 3.4 (20)* |

Number of cells of control: 0.5548 $10^6$ disk ± 0.05 (55) ($\bar{x}$ ± SEM (n))

Groups of five Wistar rats of weight 180-200 grams are treated for a period of seven days with 0.1, 1.0 and 10 mg of P/kg of the following biphosphonic acids:

difluoromethanebiphosphonic acid ($F_2MBP$) (in the form of Na salt);

4-amino-1-hydroxybutanbiphosphonic acid ($AHB_UBP$);
5-amino-1-hydroxypentanbiphosphonic acid ($AHP_EBP$);
6-amino-1-hydroxyhexanebiphosphonic acid ($AHE_XBP$);
dichloromethanebiphosphonic acid ($Cl_2MBP$) (in the form of the sodium salt) (1 mg of P/kg).

The animals kept as a control were administered the solvent with NaCl. All the treatments were carried out by the subcutaneous route. The compounds were dissolved in NaCl for the two lower concentrations and in water for the higher concentration and were administered in a volume of 0.2 ml/100 g. The animals were fed with Altromine 1314 containing 1.1 g/100 g P and 250 IU/100 g of vitamin $D_3$. On the eighth day, the animals were killed and the tibia was removed and fixed in 50% ethanol. The tibiae were then dehydrated in increasing concentration of ethanol and allowed to soak in methylmethacrylate after the addition of Plastoid N. Frontal sections were removed and cut to a thickness of 70-80 μm and then the sections were submitted to microradiography. This procedure permitted to evaluate the density of the mineral in the trabecular metaphysis accord- By reference to the production of the lactate $Cl_2MBP$ diminishes it as it is well known. On the other hand, $F_2MBP$ has no effect. The amino derivatives exhibit increase in the production of the lactate, a fact which is more pronounced with the compounds with odd number of carbon atoms. The data are reported in Table 4.

TABLE 4

| Compound | Effect on the production of lactate ± S.E.M. (n) % of control concentration (μM) | | |
|---|---|---|---|
| | 2.5 | 25 | 250 |
| $Cl_2MBP$ | 87.5 ± 4.0 (4)* | 67.1 ± 2.8 (12)*** | 16.9 ± 2.2 (12)*** |
| $F_2MBP$ | 112.1 ± 4.4 (12)* | 106.2 ± 3.9 (12) | 99.7 ± 4.7 (16) |
| $AHB_UBP$ | 88.0 ± 1.5 (8)* | 79.6 ± 4.1 (7)*** | 179.8 ± 18.6 (15)** |
| $AHP_EBP$ | 93.4 ± 3.0 (8) | 354.1 ± 27.7 (16)*** | dead cells |
| $AHE_XBP$ | 109.4 ± 6.0 (8) | 108.3 ± 4.5 (8) | 164.7 ± 7.7 (20)*** |

+ In one experiment, the number of cells was 51.2% of the control, in three experiments, it was 1-3%. These concentrations represent the limit at which the cells die.
Production of lactate: 3.83 μMol/$10^6$ cells ± 0.10 (55) ($\bar{x}$ ± SEM (n))

Experiments on the bone reabsorption and calcification in vivo

One animal per group has been evaluated. The data are reported in Table 5.

TABLE 5

| | Effect on the bone readsorption and mineralization of bones | | |
|---|---|---|---|
| Compound | Dose (mg) | Readsorption | Mineralization |
| $F_2MBP$ | 10 | — | — |
| | 1 | — | — |
| | 0.1 | — | — |
| $AHB_UBP$ | 10 | +++ | −/+ |
| | 1 | ++/+++ | — |
| | 0.1 | + | — |
| $AHP_EBP$ | 10 | Experiment interrupted due to acute toxicity | |
| | 1 | +++ | — |
| | 0.1 | +++ | — |
| $AHE_XBP$ | 10 | * | +++ |
| | 1 | ++ | — |
| | 0.1 | — | — |
| $Cl_2MBP$ | 1 | +/++ | — |

− = no inhibition of the readsorption or mineralization
Between + and +++ = increase in the inhibition of reabsorption or mineralization
* = effect not established due to inhibition of mineralization It appears that AHP$_E$BP is the most active in inhibiting the bone reabsorption. However, there is observed a toxicity at the higher dosage. The substances AHP$_U$BP and AHE$_X$BP are also active on the reabsorption with a result slightly superior to Cl$_2$MBP. A significant difference is with respect to the mineralization because AHE$_X$BP induces strong inhibition of mineralization in the dose of 10 mg of P/kg while AHB$_U$BP has no effect or only a slight effect or only an effect to a very small extent.

These results show that the amino compounds with an odd number of carbon atoms are somewhat toxic but are much more active in inhibiting the bone reabsorption. The compounds with an even number of carbon atoms have an activity slightly superior to Cl$_2$MBP. Another significant fact is that AHB$_U$BP does not induce or induces only to a very small extent the inhibition of mineralization at high dosage while AHE$_X$BP exhibits high inhibition. Consequently, AHB$_U$BP appears to be more suitable for use in diseases with an increase reabsorption of bone in humans. Finally, it is interesting to note that F$_2$MBP has no effect on the bone reabsorption or on the bone mineralization and in view of the fact that it inhibits the growth in vitro of the crystals of apatite, it may be used successfully in conditions of urolithiasis.

In fact, for a long time, a biphosphonate capable of inhibiting the growth of the crystals without affecting the bone has been the subject of research. It is concluded, therefore, that the two substances AHB$_U$BP and AHP$_E$BP are destined to become medicaments capable of inhibiting the bone reabsorption and that F$_2$MBP is useful for the treatment of urolithiasis.

CLINICAL TESTS USING ABDP

The substance ABDP, aminobutanediphosphonate has been used for venous infusion, 0.5–25 mg/day dissolved in 500 cc of 5% glucose solution in the following conditions:

1. Primary Hyperparathyroidism

Eight individuals having different degrees of calcemia varying to the extent of 17–11 mg%, were treated. In seven patients who had very elevated calcemia values which had affected the bones not only from the bioumoral but also radiographic point of view, a drastic reduction of calcemia was achieved up to normal values in five of the patients. The decrease of calcemia has been obtained simultaneously with a rapid and parallel decrease of hydroxyprolinuria and decrease of the values of the urinary excretion of calcium. In three cases, the administration of 25 mg/day of the substance for seven days has brought the normalization of calcemia up to the day of surgical intervention of removal of the parathyroidal adenoma which occurred 15–90 days after the end of the therapeutical cycle with ABDP. In the other four patients treated for shorter period of time, only 3–4 days and with a dose of 4–8 mg/day, the decrease of calcemia has been transitory, with the values of calcemia and the hydroxyprolinuria having a tendency to return to the basal values a few days after the suspension of the drug.

Only in one case with border line values of calcemia and no symptoms of the bone having been affected, the administration of 4 mg/day of ABDP for a period of four days has not caused any variation in the calcemia even if it is accompanied by a persistent reduction in the calcemia. The comparison of the results obtained in patients with primary hyperparathyroidism using Cl$_2$MDP (Adami et al, Calcif. Tissue Int. 1983) and ABDP leads to the conclusion that ABDP is 20–100 times more active than Cl$_2$MDP, in spite of the allowance which must be made due to the variation of clinical symptoms from patient to patient.

2. Paget's Disease

Three patients have been treated with ABDP in the dose of 4 mg. in one patient and 0.5 mg in the case of the other two patients, per day, for a period of 8 and 21 days respectively. In all the three patients, there has been obtained a normalization of the urinary excretion of hydroxyproline. The alkaline phosphatemia has undergone a gradual decrease up to normal values after 3–4 months of therapeutic cycle. After 6–8 months, the three patients still exhibit normal values of hydroxyprolinuria and alkaline phosphatemia.

3. Neoplastic Hypercalcemia

The experiments with ABDP relate to a single case of an individual to whom 8 mg/day for a period of two days was administered and who showed a decrease of calcemia from 14–9 mg% in the course of 48 hours.

4. Neoplastic Osteolysis

Six patients who had widespread neoplastic osteolysis have been treated with 4 mg/day for a period of two weeks. In every case, there is observed the normalization of calciuria and there is observed a consistent decrease (50–80%) of hydroxyprolinuria in five days. The painful bone symptoms have decreased after 5–8 days treatment.

In conclusion ABDP has shown to be a substance with definite properties of inhibition of the bone reabsorption, about 100–300 times more active than Cl$_2$MDP. The two substances differ also with respect to the mechanism of action: the activity on the immunity system appears to be peculiar to ABDP in spite of the fact that detailed observations in this respect in comparison with the phosphonates are not available yet. In conclusion, ADBP surprisingly has shown to be the most powerful diphosphonate for clinical use and this substance permits to carry out an effective treatment of diseases with dosages substantially lower as compared to the other bisphosphonates, which doses are perfectly tolerated by the patients.

Similar results have been obtained in another study in which two patients with tumoral osteolysis have been treated for three days with 50 mg of AHB$_U$BP. It has been remarkably noted in both cases that the treatment has been surprisingly every effective and also, it has been noted that the period of remission of the symptoms following the treatment has been surprisingly long.

The administration of AHB$_U$BP has also been remarkable in the sense that it has not been followed by fever, a fact which, on the other hand, occurs very frequently as a result of the administration of the other bisphosphonates such as the amino-hydroxy-propandiphosphonate. This fact also shows that even small structural differences may cause unforeseen modifications in the activity and tolerability.

The pharmaceutical compositions according to the present invention may be prepared for use in the form of capsules or tablets or in solution for oral administration or for systemic use. The compositions are advantageously prepared together with inert carriers such as sugars (saccharose, glucose, lactose), starch and derivatives, cellulose and derivatives, gums, fatty acids and their salts, polyalcohols, talc, aromatic esters.

Some typical pharmaceutical formulations containing amino-butan-diphosphonic acid are shown herebelow:

TABLE 6

|  | 1 | | 2 | |
|---|---|---|---|---|
| OPERCOLATED CAPSULES | | | | |
| 4-amino-1-hydroxybutan-1,1-biphosphonic acid, sodium salt | mg. | 25.0 | mg. | 12.5 |
| Lactose | | 84.0 | | 80.0 |
| Hydrolyzed Starch | | 5.0 | | 5.0 |
| Talcum | | 5.0 | | 8.5 |
| Magnesium Stearate | | 1.0 | | 1.0 |
| | Total Weight | 120.0 | | 107.0 |
| EFFERVESCENT GRANULATES | | | | |
| 4-amino-1-hydroxybutan-1,1-biphosphonic acid | mg. | 10.0 | | |
| Anhydrous Sodium Carbonate | | 12.0 | | |
| Sodium Bicarbonate | | 63.0 | | |
| Anhydrous Citric Acid | | 110.0 | | |
| Sodium Saccharinate | | 5.0 | | |
| Saccharose | mg. | 493.0 | | |
| Dehydrated Lemon Juice | | 55.0 | | |
| Natural Essence of Lemon | | 2.0 | | |
| | Total Weight | 750.0 | | |
| FORMULATIONS SUITALE FOR INJECTION | | | | |
| 4-amino-1-hydroxybutan-1,1-biphosphonic acid | mg. | 0.5 | mg. | 1.00 |
| Sodium Hydroxide | | 0.25 | | 0.25 |
| Sodium Chloride | | 8.40 | | 16.30 |
| Purified Water q.b. | ml. | 1.0 | ml. | 1,2.0 |

PHARMACOLOGY

The substance AHBuBP has been compared with a series of several other phosphonates after a treatment in vivo in rats using as parameter of activity the ability of inhibiting the bone reabsorption. The results obtained surprisingly show that the substance, the amino-butane derivative AHBuBP exhibits an activity about 100 times superior to that exhibited by amino-hydroxy-propane-diphosphonate, AHPrBP, and between 100 and 1000 times superior to that of sodium chlodronate Cl$_2$MBP and some of the biphosphonates which, up to present, have been considered the most active.

If one considers the pharmacological activity together with the degree of toxicity of the substance which remains similar and comparable to that of the other diphosphonates, one concludes that AHBuBP remarkably may offer a substantial advantage from a clinical point of view with respect to the substances used as a comparison. One must also consider that this surprisingly high activity could not have been foreseen on the basis of the chemical structure insofar as it has been amply demonstrated that even small structural variations result in substantial differences from the point of view of activity as well as tolerability of the substances. In the table hereinbelow, Table 7, there are shown the results of the change of structure of four amino-bisphosphonates namely, 3-amino-1-hydropropylidene-1,1-bisphosphonate to 6amino-1-hydroxyhexylidene-1,1-bisphosphonate with respect to the metaphyseal bone density which is quantitatively analyzed with "Quantimed". The table gives local skin toxicity which is evaluated on the basis of the necrosis. The most toxic substance is the 3-amino-1-hydroxypropylidene-1,1-bisphosphonate. Table 8 gives the effect on the bone density. The values in the table show that the propane, pentane and hexane compounds exhibit about the same degree of potency, but 4-amino-1-hydroxybutylidene-1,1-bisphosphonate is about 10 to 100 times more active if administered subcutaneously. This higher activity is also exhibited when the drug is administered orally.

The results, therefore, show that 4-amino-1-hydroxybutylidene-1,1-bisphosphonate is the most valuable of the four compounds because it possesses the highest inhibitory activity on bone reabsorption. Actually, the substance exhibits an activity which is the highest of all the bisphosphonates known up to present. In addition, the substance exhibits a topical skin toxicity which is lower than that of the 3-amino-1-hydroxypropylidene-1,1-bisphosphonate, which is the substance presently used clinically.

TABLE 7

| Amount in mg P/kg | 0.01 s.c. | 0.1 s.c. | 1.0 s.c. | 10.0 s.c. | 2.0 p.o. |
|---|---|---|---|---|---|
| NaCl Controls | | 29.72 (17) ± 3.82 | | | 28.45 (12) ± 3.22 |
| Cl$_2$MBP | | 38.21 (6) ± 5.31 | 47.00 (6) ± 4.69 | 52.65 (6) ± 5.64 | 31.20 (8) ± 2.45 |
| AHPrBP | 39.53 (7) ± 3.60 | 50.31 (6) ± 5.08 | — | — | 33.72 (6) ± 6.51 |
| AHBuBP | 48.96 (7) ± 3.82 | 58.17 (5) ± 2.55 | 60.00 (4) ± 5.78 | — | 43.80 (7) ± 10.48 |
| AHPeBP | 37.85 (7) ± 5.03 | 50.44 (6) ± 5.36 | 56.47 (6) ± 4.08 | — | 38.70 (6) ± 6.15 |
| AHHexBP | 38.12 (7) ± 1.95 | 46.96 (5) ± 5.32 | 54.93 (5) ± 5.91 | — | 34.69 (9) ± 7.38 |

Effect of various aminobisphosphonates administered for 7 days to rats on the metaphysical density (% volume of calcified tissue).

The results of necrosis at the injection sites in rats treated with several aminobisphosphonates are shown in Table 8 hereinbelow in which the symbol "n" means the number of treated animals, the symbol ∅ means that no necrosis has occurred. The symbol "x" represents a conventional score, that is "x" meand slight necrosis, "xx" means severe necrosis, "xxx" means very severe necrosis.

TABLE 8

| | | 1 day | 2 day | 3 day | 4 day | 5 day | 6 day | 7 day | 8 day |
|---|---|---|---|---|---|---|---|---|---|
| AHPrBP n = 2 | 10 mg P/kg | xxx | xxx+ | | | | | | |
| AHPrBP | 1 mg P/kg | xxx | xxx+ | | | | | | |

TABLE 8-continued

|  |  | 1 day | 2 day | 3 day | 4 day | 5 day | 6 day | 7 day | 8 day |
|---|---|---|---|---|---|---|---|---|---|
| n = 2 AHPrBP | 1 mg P/kg | ∅ | ∅ | ∅ | x | x | xx | xx | + |
| n = 2 AHPrBP | 0.1 mg P/kg | ∅ | ∅ | ∅ | ∅ | x | x | x | + |
| n = 4 AHPrBP | 0.1 mg P/kg | ∅ | ∅ | ∅ | ∅ | ∅ | x | x | + |
| n = 2 AHPrBP | 0.01 mg P/kg | ∅ | ∅ | ∅ | ∅ | ∅ | ∅ | ∅ | + |
| n = 7 n = 3 | 10 mg P/kg | xx | xxx | xxx+ |  |  |  |  |  |
| AHBuBP | 1 mg P/kg | ∅ | ∅ | x | xx | xxx | xxx | stopped injection | + |
| n = 3 AHBuBP | 1 mg P/kg | ∅ | ∅ | ∅ | ∅ | ∅ | x | x | + |
| n = 2 AHBuBP | 0.1 mg P/kg | ∅ | ∅ | ∅ | ∅ | ∅ | ∅ | ∅ | + |
| n = 3 AHBuBP | 0.1 mg P/kg | ∅ | ∅ | ∅ | ∅ | ∅ | ∅ | ∅ | + |
| n = 2 AHBuBP | 0.01 mg P/kg | ∅ | ∅ | ∅ | ∅ | ∅ | ∅ | ∅ | + |
| n = 7 AHPeBP | 10 mg P/kg | xxx | xxx+ |  |  |  |  |  |  |
| n = 2 AHPeBP | 1 mg P/kg | ∅ | ∅ | ∅ | ∅ | ∅ | ∅ | ∅ | + |
| n = 4 AHPeBP | 1 mg P/kg | ∅ | ∅ | ∅ | ∅ | ∅ | ∅ | ∅ | + |
| n = 2 AHPeBP | 0.1 mg P/kg | ∅ | ∅ | ∅ | ∅ | ∅ | ∅ | ∅ | + |
| n = 4 AHPeBP | 0.1 mg/kg | ∅ | ∅ | ∅ | ∅ | ∅ | ∅ | ∅ | + |
| n = 2 AHPeBP | 0.01 mg/kg | ∅ | ∅ | ∅ | ∅ | ∅ | ∅ | ∅ | + |
| AHHexBP | 10 mg P/kg | ∅ | ∅ | x | xx | xxx | xxx | xxx | + spontaneously |
| n = 3 AHHexBP | 1 mg P/kg | ∅ | ∅ | ∅ | ∅ | ∅ | ∅ | ∅ | + |
| n = 3 AHHexBP | 1 mg P/kg | ∅ | ∅ | ∅ | ∅ | ∅ | ∅ | ∅ | + |
| n = 2 AHHexBP | 0.1 mg P/kg | ∅ | ∅ | ∅ | ∅ | ∅ | ∅ | ∅ | + |
| n = 3 AHHexBP | 0.1 mg P/kg | ∅ | ∅ | ∅ | ∅ | ∅ | ∅ | ∅ | + |
| n = 2 AHHexBP | 0.01 mg P/kg | ∅ | ∅ | ∅ | ∅ | ∅ | ∅ | ∅ | + |
| n = 7 |  |  |  |  |  |  |  |  |  |

+ - killed except in AHHexBP where animals died spontaneously

The pharmaceutical compositions can be administered by the oral route at doses from 25 to 3200 mg/die or by the parenteral route at doses from 15 to 300 mg/die of active component. Treatment is carried out for 7 days or for 3 months' periods, repeated according to needs. However, in the case of the 4-amino 1-hydroxybutan-1,1-biphosphonic acid, the pharmaceutical compositions contain the active component in an amount as low as 0.5–1.0 mg per unit dose, and usually 10–25 mgs per unit dose.

What is claimed is:

1. A method of treatment of urolithiasis and inhibiting bone reabsorption which consists of administering to a patient in need thereof an effective amount of 4-amino-1-hydroxybutane-1,1-biphosphonic acid.

* * * * *

UNITED STATES PATENT AND TRADEMARK OFFICE

CERTIFICATE EXTENDING PATENT TERM
UNDER 35 U.S.C. § 156

PATENT NO.      :   4,621,077

ISSUED          :   November 4, 1986

INVENTOR(S)     :   Sergio Rosini et al.

PATENT OWNER    :   Istituto Gentili S.p.A.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,371 days from the original expiration date of the patent, November 4, 2003, with all rights pertaining thereto as provided by 35 U.S.C. § 156(b).

I have caused the seal of the Patent and Trademark Office to be affixed this 21st day of April 1997.

Bruce A. Lehman
Assistant Secretary of Commerce and
  Commissioner of Patents and Trademarks